(12) United States Patent
Barrett et al.

(10) Patent No.: US 9,352,300 B2
(45) Date of Patent: May 31, 2016

(54) THERMALLY STABLE NANO-CATALYST

(75) Inventors: Dean Howard Barrett, Krugersdorp (ZA); Paul John Franklyn, Springs (ZA)

(73) Assignee: University of the Witwatersrand, Johannesburg, Johannesburg (ZA)

( * ) Notice: Subject to any disclaimer, the term of this patent is extended or adjusted under 35 U.S.C. 154(b) by 128 days.

(21) Appl. No.: 14/345,739

(22) PCT Filed: Aug. 19, 2012

(86) PCT No.: PCT/IB2012/054958
§ 371 (c)(1),
(2), (4) Date: Sep. 2, 2014

(87) PCT Pub. No.: WO2013/042048
PCT Pub. Date: Mar. 28, 2013

(65) Prior Publication Data
US 2014/0378299 A1    Dec. 25, 2014

(30) Foreign Application Priority Data

Sep. 19, 2012 (ZA) .................. 2011/6802

(51) Int. Cl.
*B01D 53/56* (2006.01)
*B01D 53/94* (2006.01)
(Continued)

(52) U.S. Cl.
CPC ............ *B01J 21/063* (2013.01); *B01J 23/42* (2013.01); *B01J 23/52* (2013.01); *B01J 35/002* (2013.01);
(Continued)

(58) Field of Classification Search
CPC .......... B01J 21/063; B01J 23/40; B01J 23/42; B01J 23/44; B01J 23/46; B01J 23/52; B01J 23/70; B01J 23/72; B01J 23/74; B01J 23/745; B01J 23/755; B01J 23/89; B01D 53/864; C01B 21/22; C01B 31/18; C01B 15/029; C01B 2203/1041
USPC ......... 502/326, 330, 331, 337–339, 350, 344, 502/345; 977/773, 775; 423/247, 400, 423/415.1, 584; 252/373
See application file for complete search history.

(56) References Cited

U.S. PATENT DOCUMENTS

| | | | | |
|---|---|---|---|---|
| 7,645,439 B2 * | 1/2010 | Toledo Antonio | ..... | C01G 23/04 423/609 |
| 7,759,150 B2 * | 7/2010 | Zhang | ..... | B82Y 10/00 257/419 |

(Continued)

FOREIGN PATENT DOCUMENTS

WO    WO 2008/060293    5/2008

OTHER PUBLICATIONS

Zhang et al., *Green synthesis of a self-assembled rutile mesocrystalline photocatalyst*, 12 CrystEngComm 1759-1763 (2010).
(Continued)

*Primary Examiner* — Cam N. Nguyen
(74) *Attorney, Agent, or Firm* — Buchanan Ingersoll & Rooney PC

(57) ABSTRACT

This invention relates to a titanium dioxide catalyst particle, the catalyst particle comprising rutile nanorods having metal nanoparticles deposited at or near the free ends of the nanorods, which is suitable to catalyze reactions after exposure to temperatures above 550 deg C. The invention also provides for the use of a catalyst particle in catalyzing reactions and a method of catalyzing reactions, the catalyst particle being suitable to catalyze reactions after exposure to temperatures about 550 deg C.

20 Claims, 13 Drawing Sheets

(51) Int. Cl.
| | |
|---|---|
| *B01J 8/00* | (2006.01) |
| *C01B 31/00* | (2006.01) |
| *C01B 31/18* | (2006.01) |
| *C01B 3/38* | (2006.01) |
| *C01B 21/22* | (2006.01) |
| *C01B 21/24* | (2006.01) |
| *C01B 15/01* | (2006.01) |
| *C07C 1/02* | (2006.01) |
| *C10K 1/00* | (2006.01) |
| *B01J 23/00* | (2006.01) |
| *B01J 23/02* | (2006.01) |
| *B01J 23/40* | (2006.01) |
| *B01J 23/42* | (2006.01) |
| *B01J 23/44* | (2006.01) |
| *B01J 23/58* | (2006.01) |
| *B01J 23/70* | (2006.01) |
| *B01J 23/72* | (2006.01) |
| *B01J 23/74* | (2006.01) |
| *B01J 21/06* | (2006.01) |
| *B01J 23/52* | (2006.01) |
| *B01J 35/00* | (2006.01) |
| *B01J 35/10* | (2006.01) |
| *B82Y 30/00* | (2011.01) |
| *B01J 35/06* | (2006.01) |
| *C10K 3/04* | (2006.01) |
| *C01B 3/16* | (2006.01) |
| *C01B 3/58* | (2006.01) |
| *C01B 15/029* | (2006.01) |
| *C01G 23/047* | (2006.01) |
| *C07B 33/00* | (2006.01) |
| *B82Y 40/00* | (2011.01) |

(52) U.S. Cl.
CPC ............ *B01J 35/006* (2013.01); *B01J 35/0013* (2013.01); *B01J 35/06* (2013.01); *B01J 35/1014* (2013.01); *B01J 35/1019* (2013.01); *B82Y 30/00* (2013.01); *C01B 3/16* (2013.01); *C01B 3/583* (2013.01); *C01B 15/029* (2013.01); *C01G 23/047* (2013.01); *C07B 33/00* (2013.01); *C10K 3/04* (2013.01); *B82Y 40/00* (2013.01); *C01B 2203/044* (2013.01); *C01B 2203/047* (2013.01); *C01P 2002/72* (2013.01); *C01P 2002/85* (2013.01); *C01P 2004/04* (2013.01); *C01P 2004/16* (2013.01); *C01P 2006/12* (2013.01)

(56) References Cited

U.S. PATENT DOCUMENTS 8,975,205 B2 * 3/2015 Smith ................. B01J 23/30
 502/305
9,018,122 B2 * 4/2015 Mao ................... B01J 21/063
 204/157.51

OTHER PUBLICATIONS

Akita et al., *Transmission electron microscopy observation of the structure of TiO$_2$ nanotube and Au/TiO$_2$ nanotube catalyst*, 37 Surf. Interface Anal. 265-269 (2005).

Ren et al., *Preparation and characterization of doped TiO$_2$ nanodandelion*, 61 Materials Letters 427-431 (2007).

Zhao et al., *Preparation characterization of Au (or Pt)-loaded titania nanotubes and their photocatalytic activities for degradation of methyl orange*, 255 Applied Surface Science 3773-3778 (2009).

* cited by examiner

THERMALLY STABLE NANO-CATALYST

BACKGROUND OF THE INVENTION

THIS invention relates to a catalyst particle comprising a titanium dioxide rutile nano support structure loaded with metal nanoparticles that is catalytically active for multiple chemical reactions across a wide range of temperatures after exposure to high temperatures for prolonged periods of time. In particular, but not exclusively, this invention relates to a catalyst particle comprising a support structure of titanium dioxide rutile nanorods extending radially from a central point, wherein the nanorods are loaded with gold (Au) nanoparticles, the catalyst being catalytically active from below room temperature to high temperatures after exposure to temperatures in excess of 550° C. for prolonged periods of time.

Supported Au nanocatalysts are known to have very high activities in a number of important industrial reactions, including oxidation of CO and hydrocarbons, reduction of $NO_x$, water-gas-shift reaction, $H_2O_2$ production from $H_2$ and $O_2$, removal of CO from hydrogen steams, and selective epoxidation as well as oxidations. Further known uses of nanogold catalysts include oxidation of propylene to propylene oxide, combating pollution as welt as prolonging the life of hydrogen fuel cells. The remarkable performance of gold-based catalysts in CO oxidation spurred scientists to test these catalysts in other oxidation reactions, such as the epoxidation of alkenes, oxidative destruction of hydrochlorides, and oxidation of $CH_4$. Many of these aforementioned reactions are currently catalysed by metals from the platinum group metals (PGM's).

Haruta et al. reported (M. Haruta, N. Yamada, T. Kobayashi and S Iijima, *J. Catal.*, 115, (1989), 301) that supported nanogold is able to catalyse the oxidation of carbon monoxide at temperatures as low as −70° C. Au catalysts therefore have the potential to catalyse other reactions which are currently catalysed using PGM's, such as in autocatalysts. Nanogold catalysts are able to catalyse exhaust gas streams at much lower temperatures than current PGM based catalysts. When the CO oxidation reaction is considered the rate of oxidation of CO for Au catalysts is more than one order of magnitude higher than those for similarly prepared platinum catalysts. In other words, Au based autocatalysts are able to catalyse exhaust emissions from very low temperatures avoiding higher light off temperatures suffered by current PGM based catalysts. This exceedingly high activity of Au catalysts for CO oxidation has been a subject of great interest in the catalysis community.

The other feature of the low temperature activity is the use of Au catalysts in CO filters for gas masks and air scrubbers. In this application a catalyst is required that does not lose activity with time and is able to operate at high efficiency at low temperatures.

Such activity is unique to supported Au nanoparticles, however it only occurs if the supported Au nanoparticles are smaller than 8 nm in size, with optimal activity attained at around 5 nm or smaller.

Furthermore, both the activity and the selectivity of the catalyst is dependent on the Au particle size as well as the support used to hold the Au. However, the direct applications of supported Au nanocatalysts to the above industrial processes, including autocatalysts, have been hampered by the instability of the Au nanocatalysts against sintering under extreme reaction conditions and also under standard conditions over prolonged time periods.

Accordingly, ultra stable supported Au nanocatalysts that are particularly impervious to high temperature treatments in any atmosphere are extremely desirable to industrial applications because most of the aforementioned reactions proceed at relatively high temperatures. In addition, in the case of autocatalyst applications, catalyst activity also needs to be maintained at low temperatures thereby avoiding pollution created while the engine is cold, before the current Pt based catalysts reach their light-off temperature. In addition, in the case of filter masks the catalyst needs to remain active after long periods of shelf life—often in non-ideal conditions.

The literature indicates that current supported Au based catalysts intended for high temperature applications, i.e. over 450° C., are only calcined for a short amount of time and then tested for catalytic activity. Further, many of the catalysts are bi- or tri-metallic catalysts with Au forming the minor component and PGM's the major.

Two important, but distinctly different, factors have been suggested to be important for the control of the activity of Au catalysts; firstly Au particle size, and secondly support effects.

The correlation between activity and Au particle size has been clearly demonstrated for Au nanoparticles supported on reducible metal oxides and it is generally accepted that the high catalytic activity of supported Au catalysts in low temperature CO oxidation can be accredited to the presence of small Au crystallites, which are stabilized by the support and where the strong interaction with the support helps to create a favourable electronic environment to promote the activity of the Au.

Furthermore, the support interface has also been shown to play an important role in the catalysis. In order to try and stabilise gold nanoparticles for high temperature applications various supports, including $TiO_2$, $Al_2O_3$, $CeO_2$, ZnO, $SiO_2$, $ZrO_2$, and $Co_3O_4$ as well as combinations of these, have been used to test Au for the catalytic oxidation of CO. Of all of these, $TiO_2$ in the anatase phase has been found to be one of the most active, and has been extensively used for a number of years as it is known to be highly active with Au for the oxidation of CO. Titania is in a class of supports known as active supports due its ability to be easily reduced and facilitate the transfer of oxygen between the support and the Au. This is further improved by the effect of its isoelectric point on the deposition of Au nanoparticles to form strong bonds with the $TiO_2$ support.

Anatase has long been the preferred phase of $TiO_2$ when considering possible supports for various reactions due to its large surface area when compared to rutile's 7.2 $m^2$/g average surface area. However, the limiting factor for both anatase and P25 is the conversion of anatase to the thermodynamically preferred rutile phase which results in a massive loss of catalytic activity. This conversion is driven by temperature and is affected by the presence of the Au on the support.

A significant amount of research has been conducted on attempting to stabilise Au nanoparticles for higher temperature applications such as automotive catalysts.

An article by Mellor et. al. (Mellor J. R, Palazov A. N, Grigorova B. S, Greyling J. F, Reddy K, Letsoalo M. P, Marsh J. H, (2002) Catal. Today 72:145) a catalyst containing Au on cobalt oxide particles supported on a mixture of zirconia-based ceria, zirconia and titania was able to survive 157 hours at 500 deg C. However, a large loss of activity and a large loss of support surface area were reported.

In work developed by Seker and Gulari, $Au—Al_2O_3$ catalysts were able to survive pre-treatments at 600 deg C. in air for 24 hours followed by several cycles of 150-500 deg C. The catalysts were then kept at 500 deg C. for 12 hours and showed high activities for NO conversion. However, NO conversion is less sensitive to Au particle size changes compared to the CO oxidation reaction implying the catalyst may have undergone deactivation for the CO oxidation reaction while still remaining active for NO conversion. No information was provided as to the catalyst's ability to oxidize CO. Much like the Mellor catalyst discussed above, the temperatures that the catalysts were exposed to were not significantly high when the duration of exposure was considered.

EP 1 043 059 to Toyota Jidosha Kabushiki Kaisha describes a catalyst containing complex gold oxides of the form $Au_2Sr_5O_6$. In this catalyst the Au is entirely ionic and is trapped in the oxide lattice. The Toyota catalyst was tested to 800° C. for 5 hours with only a small decrease in its ability to convert $C_3H_6$ as would be found in a typical exhaust gas stream. No data for the efficiency for CO oxidation was presented.

One of the most important reasons for the development of a nanogold catalyst is due to its ability, if the Au particles remain small enough, to facilitate reactions from ambient temperatures. The Toyota patent claims a $T_{50}$ conversion at 345° C. for the fresh catalyst. This relatively high $T_{53}$ value would somewhat negate the use of nanogold, as standard PGM based auto-catalysts are also active at this temperature. Therefore, this catalyst does not address the light off period at low temperatures.

Auto-catalysts are typically produced using a mixture of PGM's. Thus, for example, a standard type auto-catalyst will be a mixture of Pt—Pd supported on corderite along with $CeO_2$. This type of catalyst has been shown to work very efficiently, but with the problem of light off at low temperatures.

U.S. Pat. No. 7,709,407 describe a method for producing a supported catalyst containing palladium-gold metal particles. The addition of Au is claimed to reduce the light off temperature and hence the catalyst is able to catalyse reactions from very low temperatures. However, if the catalyst reaches any significantly high temperature the stability of the Au nanoparticles must be called into question as Au supported on zeolites has been shown to be an unstable combination at high temperatures. No information on the durability of the catalyst after exposure to high temperatures was revealed. However, the catalyst was designed for diesel internal combustion engines where the exhaust gas temperatures are relatively mild when compared to gasoline engines.

If Au catalysts are to be used in applications above 400° C., such as in automotive catalysts, thermal stability of not only the Au nanoparticles but also the stability of the support is crucial for long term activity. It has been reported that, in a European driving cycle, temperatures average between 80-450 deg C., while in the extra urban part of the cycle average temperatures of 200-450 deg C. can be expected. Some Au catalysts may cope with these temperatures, however at certain times during the cycle temperatures may reach well over 500 deg C. and enter a thermal region that current Au based catalyst cannot operate in. In addition, prolonged and repeated expose to such temperatures will inevitably deactivate the Au.

Therefore, there remains a need for a catalyst that can meet the requirements of both thermal stability and durability, to be considered as a potential catalyst for reactions undertaken at temperatures from below ambient to above 550° C. for prolonged periods of time.

There remains a further need for an Au catalyst that can meet the requirements of both thermal stability and durability, to be considered as a potential catalyst for reactions undertaken at temperatures from below ambient to above 550° C. for prolonged periods of time.

SUMMARY OF THE INVENTION

According to a first aspect of the invention there is provided a titanium dioxide catalyst particle comprising rutile nanorods extending radially from a central point, each nanorod having a free end spaced from adjacent nanorods, the particle including metal nanoparticles deposited at or near the free ends of the nanorods, wherein the particle is suitable to catalyse reactions after exposure to temperatures above 550 deg C.

In one embodiment the catalyst particle has a BET surface area of between about 50 and about 125 $m^2/g$.

Preferably, the catalyst particle has a BET surface area of between about 75 $m^2/g$ and about 115 $m^2/g$.

Most preferably, the catalyst particle has a BET surface area of about 100 $m^2/g$.

The catalysed reaction may be selected from a list of reactions including the oxidation of CO, oxidation of hydrocarbons, reduction of $NO_x$, water-gas-shift reaction, $H_2O_2$ production from $H_2$ and $O_2$, removal of CO from hydrogen steams, epoxidation of alkenes, oxidative destruction of hydrochlorides, and/or the oxidation of $CH_4$.

In a preferred embodiment the catalysed reaction is the oxidation of CO.

The catalyst particle may have a substantially spherical dandelion shaped configuration.

Preferably, the nanorods are of substantially similar length.

The nanorods may be comprised of substantially phase pure rutile.

The metal nanoparticles may be metal nanoparticles of one or more metals selected from the group consisting of gold, cobalt, nickel, copper, iron, zinc, silver, platinum, palladium, ruthenium, rhodium, osmium, iridium, molybdenum, and/or alloys thereof.

Preferably, the metal nanoparticles are metal nanoparticles of one or more metals selected from the group consisting of gold, platinum, palladium, ruthenium, rhodium, osmium, iridium, and/or alloys thereof.

Most preferably, the metal nanoparticles are gold nanoparticles.

The metal nanoparticles may be present at loadings of between about 0.1% and about 10% by weight of the particle.

Preferably, the metal nanoparticles are present at loadings of between about 0.5% and about 5% by weight of the particle.

Most preferably, the metal nanoparticles are present at loadings of about 1%.

The catalyst particle preferably has a CO oxidation conversion at about 50 deg C. of more than 50%, compared to the CO oxidation conversion of an unheated catalyst particle, after heating at a temperature of between about 450 deg C. and about 800 deg C. for at least 24 hours.

More preferably, the catalyst particle has a CO oxidation conversion at about 50 deg C. of more than about 65%, compared to the CO oxidation conversion of an unheated catalyst particle, after heating at a temperature of about 550 deg C. for at least 120 hours.

Most preferably, the catalyst particle has a CO oxidation conversion at about 50 deg C. of about 75%, compared to the CO oxidation conversion of an unheated catalyst particle, after heating at a temperature of about 800 deg C. for at about 200 hours.

According to a second aspect of the present invention there is provided a catalyst composition comprising a plurality of catalyst particles according to the first aspect of the present invention.

The catalyst particles in the composition may be fixed to a support.

In one embodiment the catalyst particles in the composition may be in solution or in suspension.

According to a third aspect of the present invention there is provided use of a catalyst particle according to the first aspect of the present invention, or a catalyst composition according to the second aspect of the present invention, to catalyse reactions, the catalyst particle having been previously exposed to temperatures above 550 deg C.

According to a fourth aspect of the present invention there is provided a method of catalysing reactions comprising the step of exposing the reagent or reagents to a catalyst particle according to the first aspect of the present invention, or a catalyst composition according to the second aspect of the present invention, the catalyst particle having been previously exposed to temperatures above 550 deg C.

BRIEF DESCRIPTION OF THE DRAWINGS

Without thereby limiting the scope, the invention will now be described in more detail with reference to the following Figures and examples in which:

FIG. 12 8% Au on $TiO_2$ rutile nanorod catalyst particles showing the crystallite sizes in the (110) and (011) directions;

FIG. 23 8% Au $TiO_2$ rutile nanorod catalyst particles heated to 810 deg C. in the in-situ PXRD data collection experiment;

DESCRIPTION OF PREFERRED EMBODIMENTS

Figure 1:
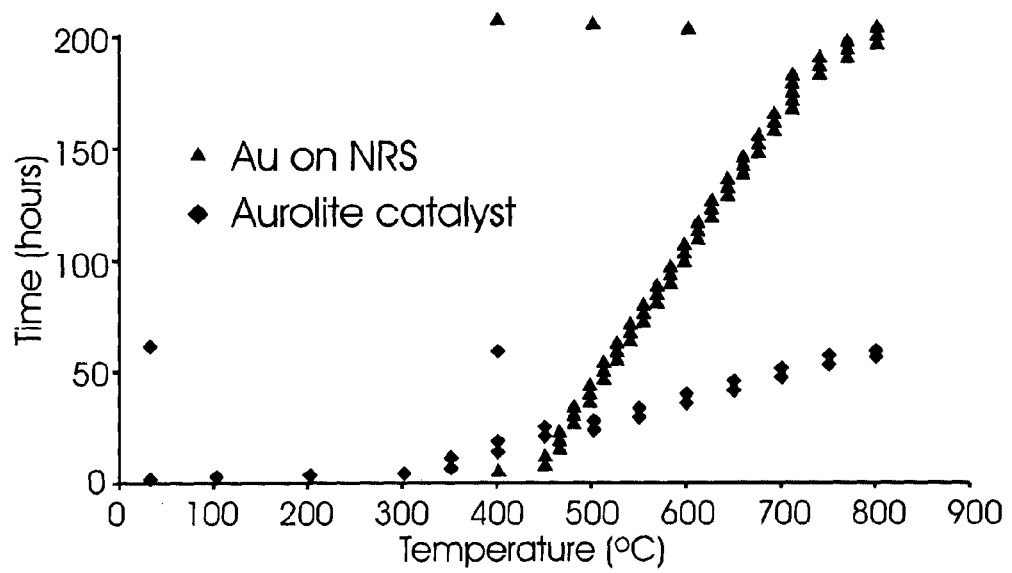
FIG. 1 shows the time versus temperature profile for in-situ powder X-ray diffraction (PXRD) data collection for Aurolite catalyst and Au loaded $TiO_2$ rutile nanorod catalyst particles.

This invention provides for a catalyst particle comprising a $TiO_2$ rutile nanorod support structure and metal nanoparticles deposited on the support.

The nanorods each have one free end that is spaced apart from an adjacent nanorod, and the metal nanoparticles are distributed at, or near, the free ends of the $TiO_2$ rutile nanorods.

The $TiO_2$ rutile nanorod support structure has a substantially spherical dandelion shaped configuration.

The term "catalyse", as used in this specification, refers to the use of a catalyst to increase the rate of a reaction.

The term "rutile", as used in this specification, refers to a polymorph of titanium dioxide, while the term "phase pure rutile" refers a to the rutile polymorph whereby only this polymorph is present, with no traces of the other titania polymorphs present.

The term "dandelion shaped" or "dandelion structure", as used in this specification, refers to a nanorod configuration having nanorods of substantially similar length extending radially from a central point of the $TiO_2$ rutile nanorod support structure. In this configuration, each one of the nanorods in the support structure has one end at, or towards, the central point of the catalyst particle, and another end, referred to as a free end, that is spaced apart an adjacent nanorod in the structure.

The term "nanorod" refers to a morphology that is elongate and has a cylindrical, rectangular, or square shape in cross-section. The term "nanowire" is used to describe a morphology that is essentially similar to the morphology of a nanorod—a nanowire only being longer than a nanorod. In this specification the term "nanorod" should be understood to incorporate the term "nanowire".

Synthesis of the $TiO_2$ Rutile Nanorod Support Structure and Catalyst Particle

The $TiO_2$ rutile nanorod support structures were synthesised via a hydrothermal reaction. 12.0 mL of $TiCl_4$ was slowly added to 160 mL of deionized water at 0 deg C. in a round bottomed flask. The solution was heated to 180 deg C. for 24 hours under reflux whilst undergoing rapid stirring.

This reaction yielded the $TiO_2$ rutile nanorod support structure in the form of a white precipitate. The white precipitate was centrifuged and washed with deionized water to remove all excess chloride ions. The solution containing the $TiO_2$ rutile nanorod support structure was repeatedly washed until the pH of the solution reached 7.

The washed white precipitate was then placed in a heating oven and dried overnight at 110 deg C. to yield the dried $TiO_2$ rutile nanorod support structure.

To load the metal nanoparticles onto the support structure a 250 mL conical flask was placed onto a temperature controlled heater stirrer and 100 mL of deionized water was added to the conical flask, 1.0 g of the product from the above described drying step was added to the deionized water. $HAuCl_4.3H_2O$, as the source of metal nanoparticles, and 0.85 M urea was added to the solution. The theoretical loading of Au was calculated to be between 1% and 8%, depending on the catalyst sample prepared.

In other embodiments, when Au—Pt metal nanoparticle loaded catalyst particles were prepared, varying amounts of $H_2PtCl_5.xH_2O$ was added to the solution.

A stirrer bar was added to the conical flask followed by the flask being sealed with the reaction undertaken in a dark fumehood so that no light could enter during the synthesis. The solution was heated to between 75 deg C. and 80 deg C. to ensure the complete hydrolysis of the urea. The reaction took place over 24 hours. Once the reaction was complete, the solution containing the catalyst particles was washed with hot deionized water and centrifuged. This process was repeated until the pH reached neutrality. Finally, the catalyst particles were placed in a drying oven overnight at 110 deg C. to remove any residual water.

Reduction was only undertaken prior to using the catalyst for either CO oxidation reactions on a catalytic testing unit, or for characterization. The $TiO_2$ rutile nanorod support structures loaded with 5% and 8% Au were produced for the in-situ powder X-ray diffraction (PXRD) characterization as well as for transmission electron microscope (TEM) studies.

For catalysis studies, $TiO_2$ rutile nanorod support structures loaded with 1% Au and $TiO_2$ rutile nanorod support structures loaded with 1% Au-x % Pt, where x=0.1 or 0.2 were produced in triplicate.

Characterization of the $TiO_2$ Rutile Nanorod Support Structure and Catalyst Particle The Brunauer-Emmett-Teller (BET) technique was used to study the surface areas of the support structures and catalyst particles produced. The method used was based on American Society for Testing and Materials (ASTM) D3663-78: Standard Test Method for surface area of catalysts, and ASTM D3908-5080: Standard Test Method for Hydrogen Chemisorption on Supported Platinum and Alumina Catalysts.

The BET setup for the data collections were as follows: The $N_2$ adsorption-desorption experiment was conducted at −193 deg C. using a Micrometrics TriStar surface area and porosity analyser. Prior to the experiment the sample was out gassed at 200 deg C. for 6 hours. The BET surface areas were obtained in a relative pressure range from 0.05 to 0.30. The total pore volume was calculated from the amount of $N_2$ vapour adsorbed at a relative pressure of 0.99.

The Rietveld refinement method is described in "The Rietveld Method by R. A. Young", Oxford Press, 1969.

The use of electron diffraction, TEM and TEM tomography confirmed that the above described synthesis method produced $TiO_2$ rutile nanorod support structures that were dandelion shaped, each nanorod being of substantially similar length and extending radially from a central point of the rutile nanorod support structure.

Surface area data was collected for the produced $TiO_2$ rutile nanorod support samples. BET results were consistent between batches, with a standard deviation of less than 15% between five batches of support produced. On average the synthesis method described above produced a support with the following characteristics:

Surface area: Single point surface area at $P/P_o$=0.09854: 95.35 $m^2/g$±11.05 $m^2/g$.

BET Surface Area: 101.90 $m^2/g$±13.15 $m^2/g$.

The standard deviation within a sample in the surface area measurements encompasses the variation noted across all the samples for the mean surface area. This implies that that variation across the samples was not statistically significant and was acceptable.

Pore Volume: Single point adsorption total pore volume of pores less than 144.4069 nm diameter at $P/P_o$=0.98641: 0.08658 $m^3/g$.

Pore Size: Adsorption average pore width (4V/A by BET): 3.398 nm.

BJH Adsorption average pore diameter (4V/A): 4.127 nm.

BJH Desorption average pore diameter (4V/A): 4.184 nm.

In-situ diffraction studies were conducted on the unloaded rutile nanorod support structure, as well as on the support structure loaded with various Au metal nanoparticle loadings.

Initial tests, whereby the $TiO_2$ rutile nanorod support structure was heated at a number of temperatures in a furnace followed by PXRD characterization, showed that the rutile nanorod support was a very stable structure. In order to thoroughly test the support as well as the catalyst particles produced using the support, data collections needed to be very long. This was necessary to thoroughly stress the catalyst particles at high temperatures.

The time versus temperature profile of the in-situ PXRD data collections is shown in FIG. 1. FIG. 1 also compares the data collection time for the commercially available Aurolite catalyst with the Au loaded $TiO_2$ rutile nanorod catalyst particles. The data collection for the Au loaded $TiO_2$ rutile nanorod catalyst particles were undertaken for a significantly longer time. The time vs. temperature profile was chosen such that over 90% of the data collections were undertaken at over 450 deg C. These collection profiles for the Au loaded rutile nanorod catalyst particle samples meant that the catalysts were exposed to temperatures exceeding 450 deg C. for almost 200 hours. The data collection at temperatures over 450 deg C. was 5 times longer for the catalyst particles produced using the rutile nanorod support structure compared to the Aurolite catalyst data collection time. The same data collection times were used for all the $TiO_2$ rutile nanorod catalysts as well as the pure $TiO_2$ rutile nanorod support structure itself.

Figure 2:
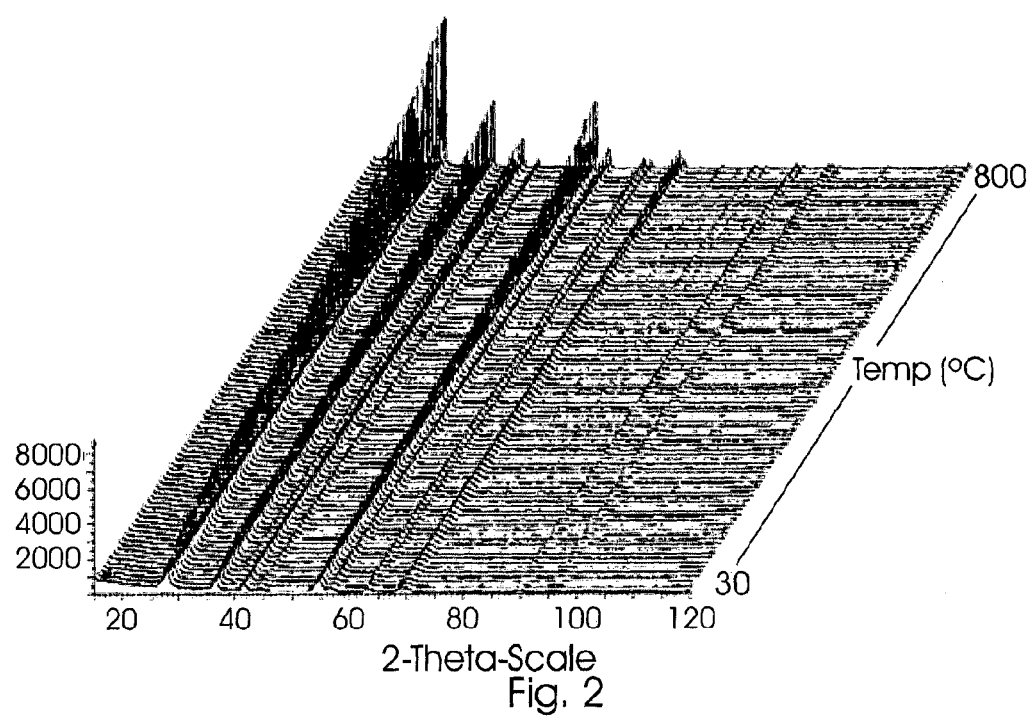
FIGS. 2 and 3 shows in-situ PXRD data for the pure $TiO_2$ ruble nanorod support.
Figure 3:
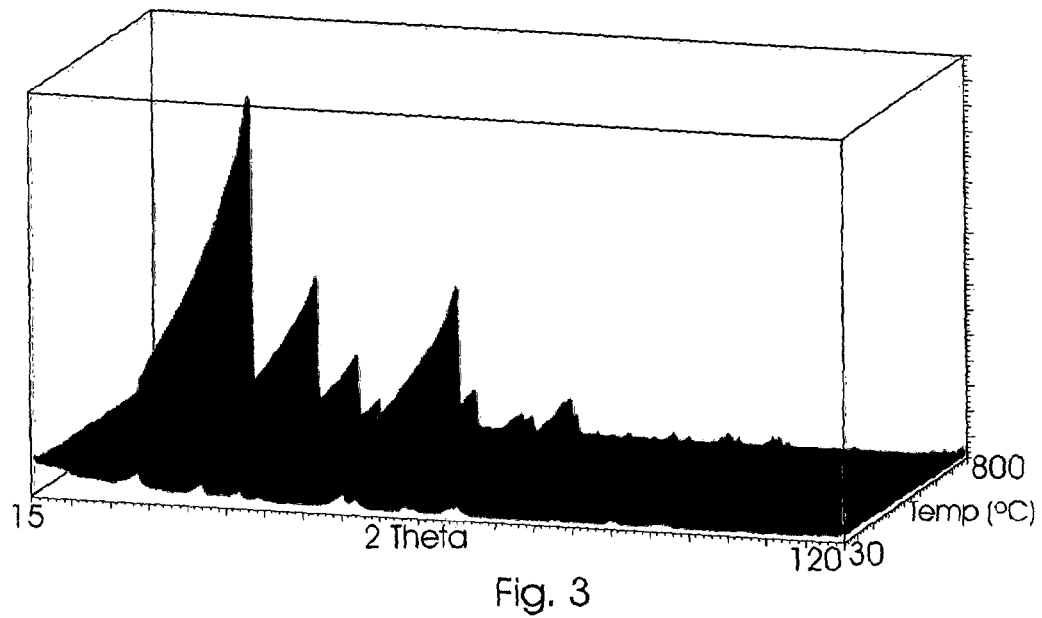

In-situ PXRD of pure $TiO_2$ rutile nanorod support showed that at high temperatures the structure was completely phase stable and, as shown in FIGS. 2 and 3, 100% of the synthesised product was thermodynamically stable nanorutile. However, in terms of the growth of the structure at high temperatures, an increase in the length of the rod structure and a general increase in the crystallite size were noted.

When even a small percentage of Au nanoparticles were added to the rutile nanorod support, the decrease in the support particle size growth with respect to temperature was dramatic.

There were two determining factors when investigating if the synthesised product produced the required support in terms of the nano characteristics of the support when using X-ray diffraction.

Examination of the (110) and (011) diffraction peaks provided information about the support's morphology as it showed the anisotropic nature of the rutile nanorod support. This pointed toward a nanorod type structure as is shown in FIG. 4.

Furthermore, the broad and somewhat low intensity of the diffraction peaks also indicated that the anisotropic nanorods were in the desired nanoscale region that confirmed the BET and TEM results of a nano support structure with high surface area. Both of these features are shown in FIG. 3, as well as quantitatively in FIG. 4.

Figure 4:
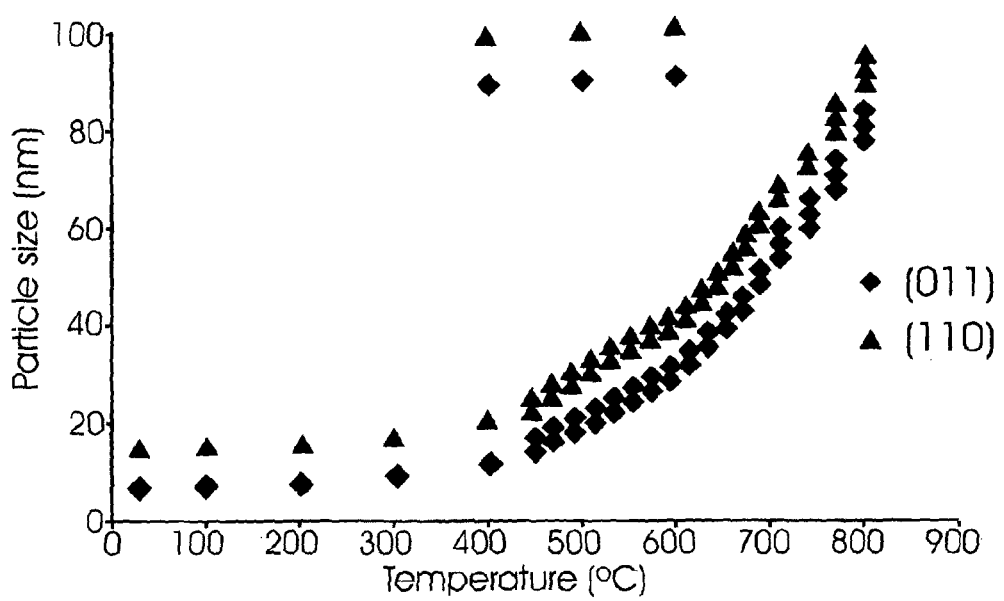
FIG. 4 shows a graph of the Rietveld refinement results of pure $TiO_2$ rutile nanorod support crystallite sizes of the (011) and (110) orientation with respect to temperature.

The difference in size of the two hkl values, as shown in FIG. 4, from Rietveld analysis applied to the in-situ PXRD data, revealed anisotropic growth along the (110) direction, Initially, the rutile nanorod support crystallite size was relatively small; however, as temperatures increased the growth of the nanostructure could be seen. The most rapid growth occurred at temperatures above 500 deg C.

As was shown using TEM and in-situ PXRD, the growth that was observed from the in-situ PXRD was primarily due to propagation and extrusion of the nanorods. Thus, as temperature increased, the nanorods extruded outward.

Figure 5:
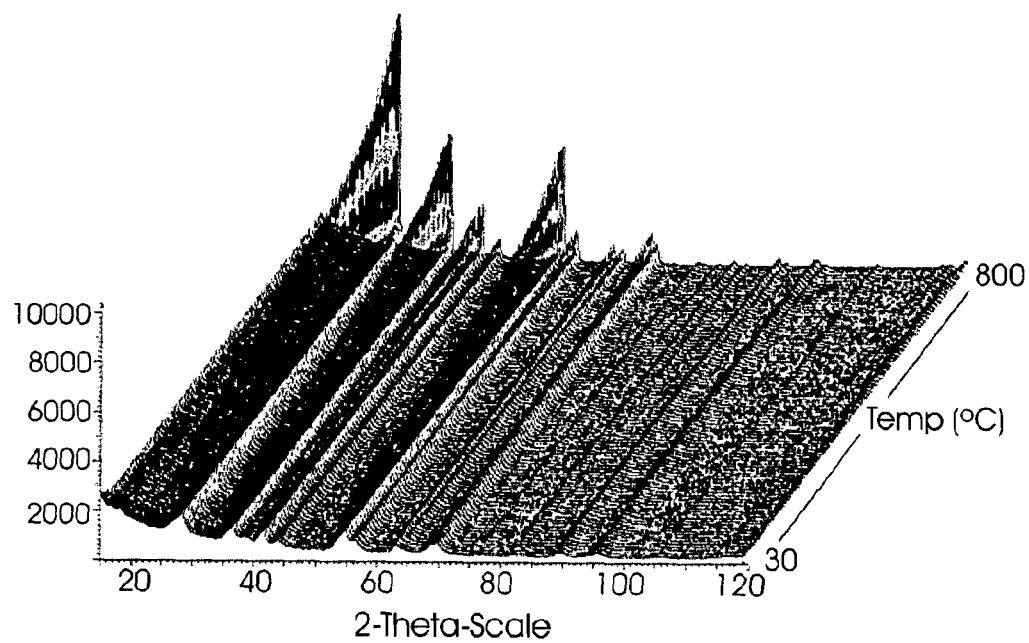
FIGS. 5 and 6 shows in-situ PXRD data for the 5% Au on $TiO_2$ rutile nanorod catalyst particles.
Figure 6:
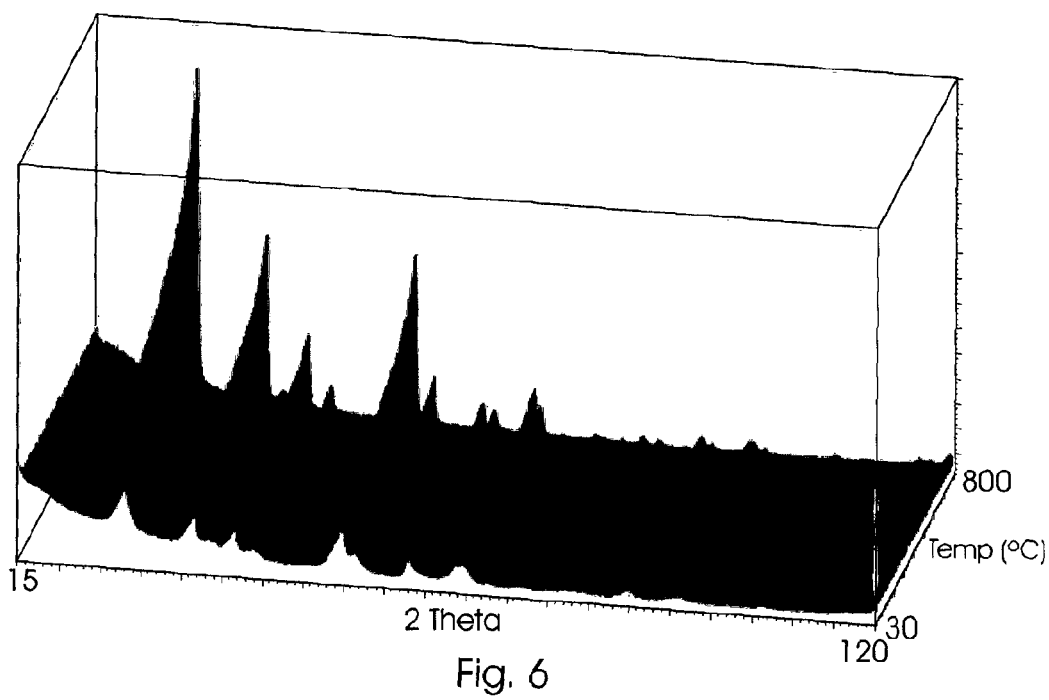
Figure 7:
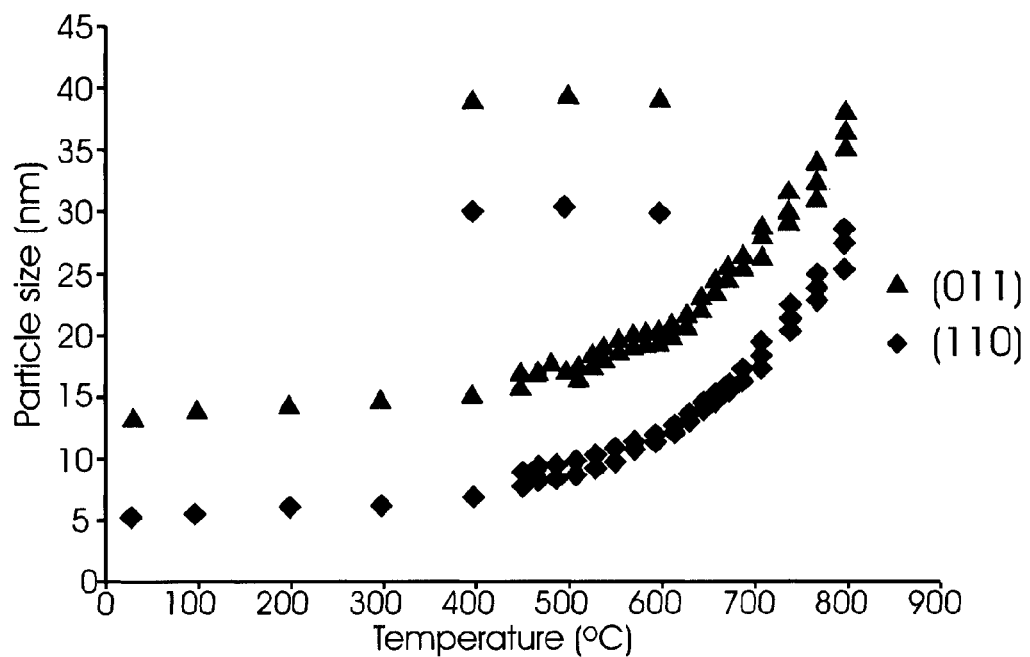
FIG. 7 shows a graph of the Rietveld refinement results for the 5% Au on $TiO_2$ rutile nanorod catalyst particles.

In in-situ PXRD studies of $TiO_2$ rutile nanorod support loaded with 5% Au, the most immediate result, when compared to pure $TiO_2$ rutile nanorod support, was a decrease in intensity at high temperature of the diffraction peaks originating from the rutile nanorod support (FIGS. 5 and 6). Rietveld refinements, shown in FIG. 7, quantitatively confirmed that the size of the nanorods was greatly decreased when 5% Au was present in nano particulate form on the rutile nanorod support, compared to the pure support after the in-situ data collection.

Thus, initial conclusions were that the Au metal nanoparticles were acting as a capping agent and inhibiting the growth of the rutile nanorods. This effect increased the stability of the support at non-ambient temperatures. Further, this effect resulted in the $TiO_2$ rutile nanorod support structure being able to retain its high surface area.

The diffraction results first indicated that the structure was dandelion shaped, as electron microscopy studies were only conducted at a later stage. This was deduced from the anisotropy of the peaks, indicating preferential growth along certain planes. Compared to the pure $TiO_2$ rutile nanorod support, the crystallite size of the structure loaded with 1% Au was less than half that of the pure support. The addition of only 3.91% Au (actual loading value from Rietveld analysis) was shown to be inhibiting the growth of the rutile nanorod structure even further.

This finding by the inventors was very important as the Au metal nanoparticles acted to stabilise the $TiO_2$ rutile nanorod support. This was a completely opposite effect compared to other supports such as P25, commercial anatase and nano anatase. These supports were detrimentally affected by the addition of Au or Pt, in that the presence of Au or Pt increased the rate of phase transformation.

Following the results of the catalyst particles produced with 5% Au loading, catalyst particles with 8% Au loading on $TiO_2$ rutile nanorod support structures were produced. The increased Au loading would allow for a more accurate crystallite size determination from the Rietveld refinements at low to medium temperatures. Due to the remarkable stability of the Au metal nanoparticles even at very high temperatures when in-situ diffraction studies were conducted on the 5% Au rutile nanorod catalyst particle sample, the diffraction peaks for Au were relatively small and almost lost in the background of the diffraction patterns. This was due to the low Au loading (3.91%) and the relatively small crystallite sizes. The need to quantitatively determine the crystallite sizes of the Au nanoparticles was seen as very important and the best method to attain this information was to increase the Au loading percentage.

Figure 8:
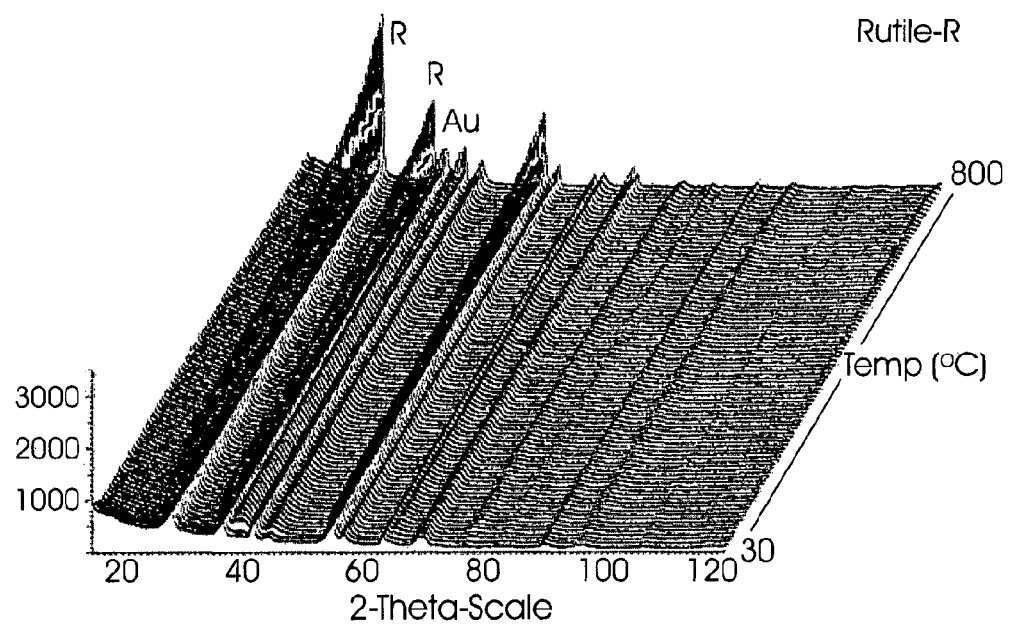
FIG. 8 shows in-situ PXRD data for the 8% Au on $TiO_2$ rutile nanorod catalyst particles.
Figure 11:
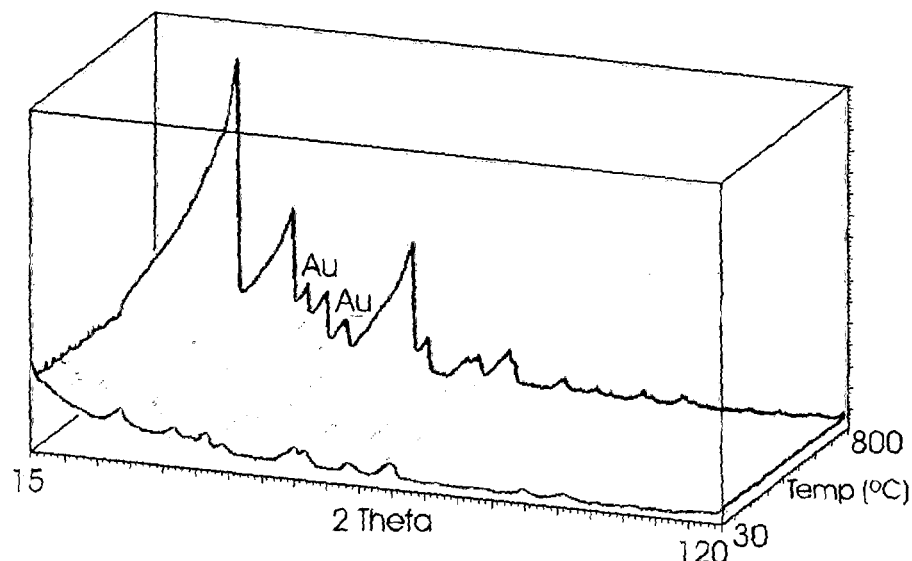
FIG. 11 shows in-situ PXRD data for the 8% Au on $TiO_2$ rutile nanorod catalyst particles showing the increase in intensity of the Au diffraction peaks.
Figure 12:
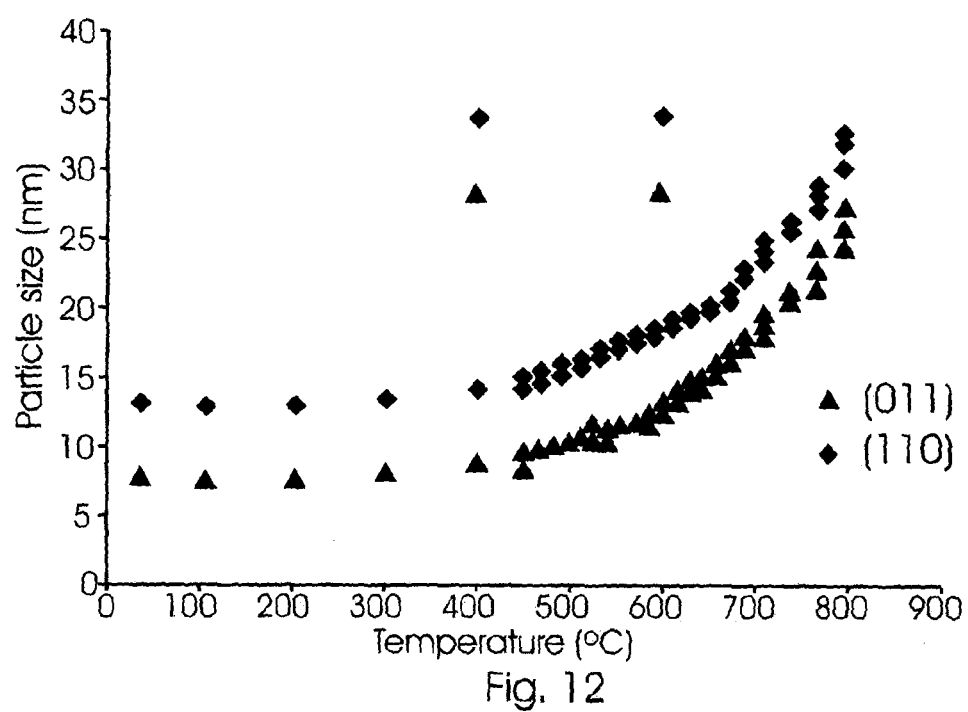
Figure 13:
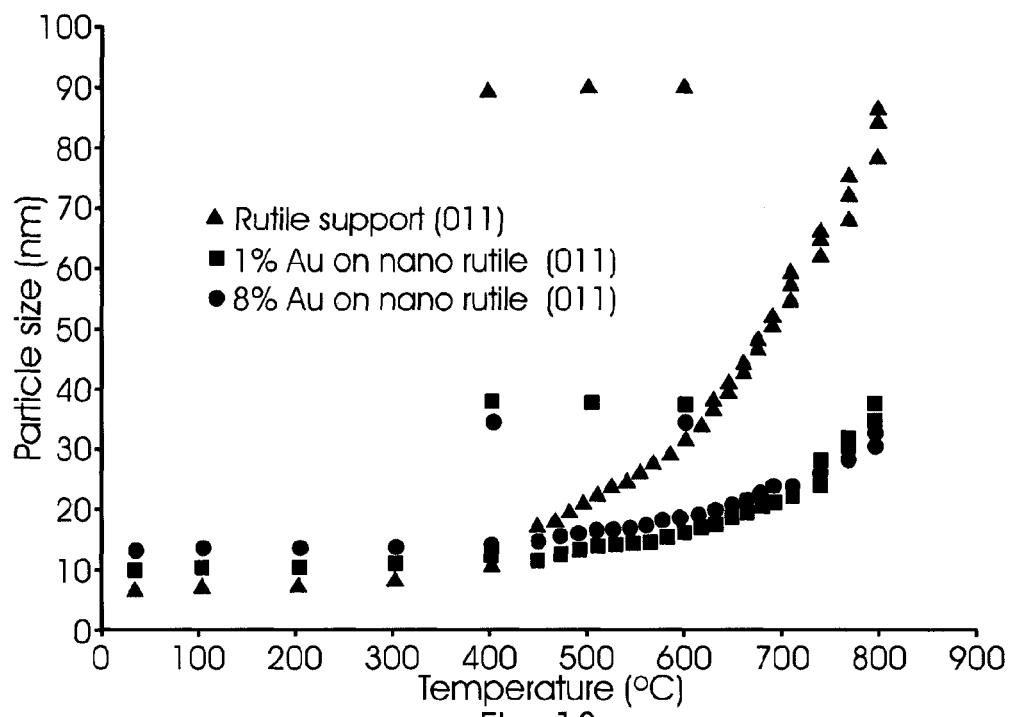
FIG. 13 Comparison of the (011) direction of $TiO_2$ rutile nanorods for the pure $TiO_2$ rutile nanorod support, 5% Au and 8% Au $TiO_2$ rutile nanorod catalyst particles.

The higher Au metal nanoparticle loading revealed the effect that extra Au nanoparticles had on the growth mechanism of the structure as shown in FIGS. 8 and 11.

Figure 9:
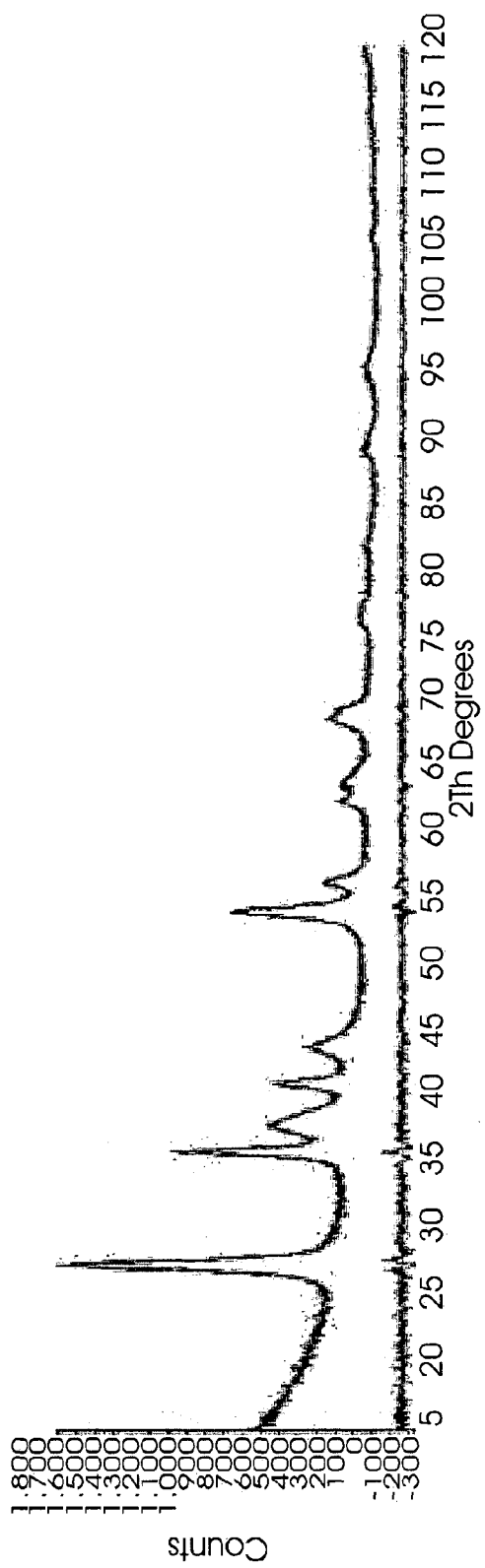
FIG. 9 shows a Rietveld refinement example of a diffraction pattern collected at 540 deg C. taken from the in-situ data collection.
Figure 10:
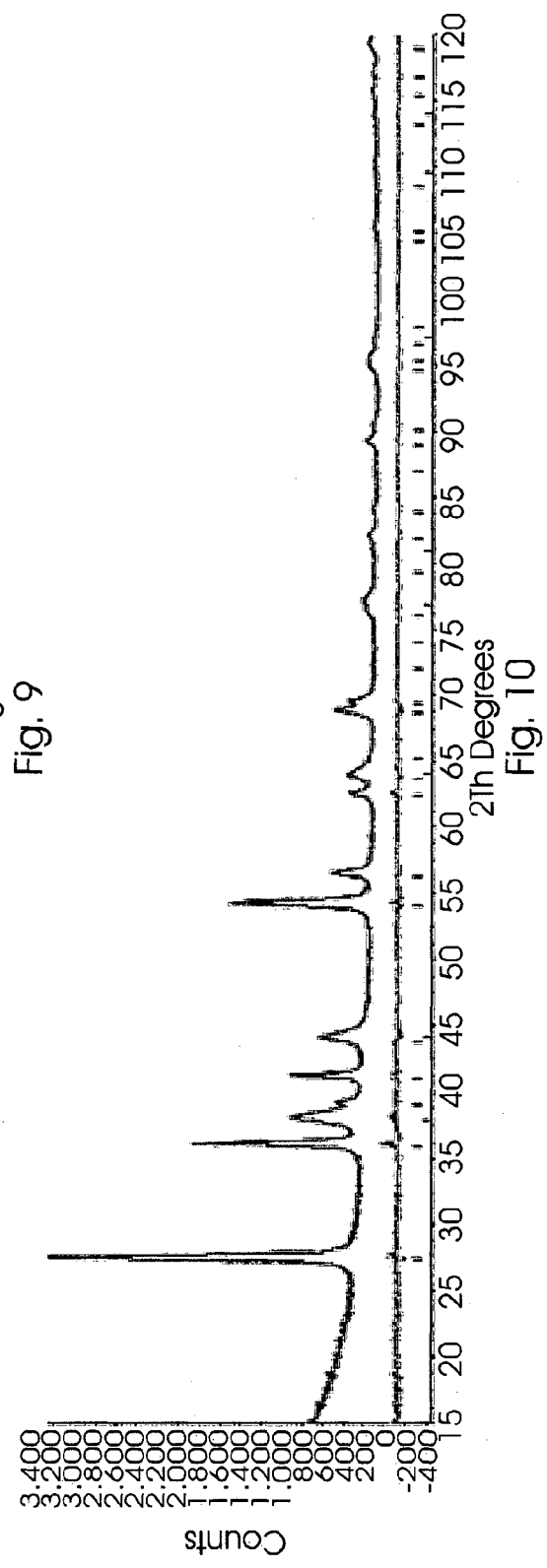
FIG. 10 shows a Rietveld refinement of the diffraction pattern collected at 540 deg C. resulting from the in-situ data collection after exposure of the catalyst particles to temperatures exceeding 450 deg C. for more than 200 hours.

Rietveld refinements gave Au loadings of 6.45% as shown in FIGS. 8-10. An Au loading below 7% was expected as not all the Au is deposited on the surface during the synthesis.

Furthermore, X-ray diffraction only detects crystalline Au. However, this value was high when compared to all the other methods available for depositing Au. High metal loadings are not desirable in active catalysts due to high metal costs. Also, with traditional catalysts, overloading of the surface leads to and enhancement of the sintering effect of the nanoparticles. The effects of overloading were not observed for the $TiO_2$ ruble nanorod support structure however, as Rietveld refinements showed small Au crystallite sizes. BET surface area studies gave a surface area of 77.4 $m^2/g$ after the in-situ data collection.

After the prolonged exposure to high temperatures this surface area was still sizeably larger than all the other commercial supports tested. By comparison the commercially available Auralite catalyst had a surface area of only 7.2 $m^2/g$ after the in-situ data collection.

After in-situ diffraction studies, for relatively shorter time periods, all the commercial titania supports and catalysts tested, had surface areas on average less than 7.5 $m^2/g$. TEM studies further demonstrated the stability of the $TiO_2$ rutile nanorod support structure after exposure to high temperatures and correlated well with the in-situ data.

The addition of Au metal nanoparticles had a direct effect on the growth of the structure at high temperatures. This growth was not thermodynamically phase driven as in the case of P25, commercial anatase and nano anatase, as the $TiO_2$ rutile nanorod support structure is already locked into its most stable titania polymorph. Thus, it was possible to slow or even stop the growth process from occurring and lock the structure in place.

Observations of the $TiO_2$ rutile nanorods before and after heating cycles indicated that the metal nanoparticles were deposited onto the ends of the rods. This was an expected result as the nanorods had small diameters (typically around 5-8 nm) and so the tips of the rods were highly strained. Therefore, if the strained environment could be protected by the presence of the metal atoms, the nanorods would become more stable.

Also, as the growth direction of the $TiO_2$ rutile crystallites was along the rod axis, preventing access to the tip of the rod would effectively prevent any growth. After exposure to temperatures in excess of 450 deg C. for over 200 hours the $TiO_2$ rutile nanorod support still remained small enough to provide high surface area (BET surface area of 77.4 $m^2/g$) for the supported metal nanoparticles to remain stable on the surface.

Figure 14:
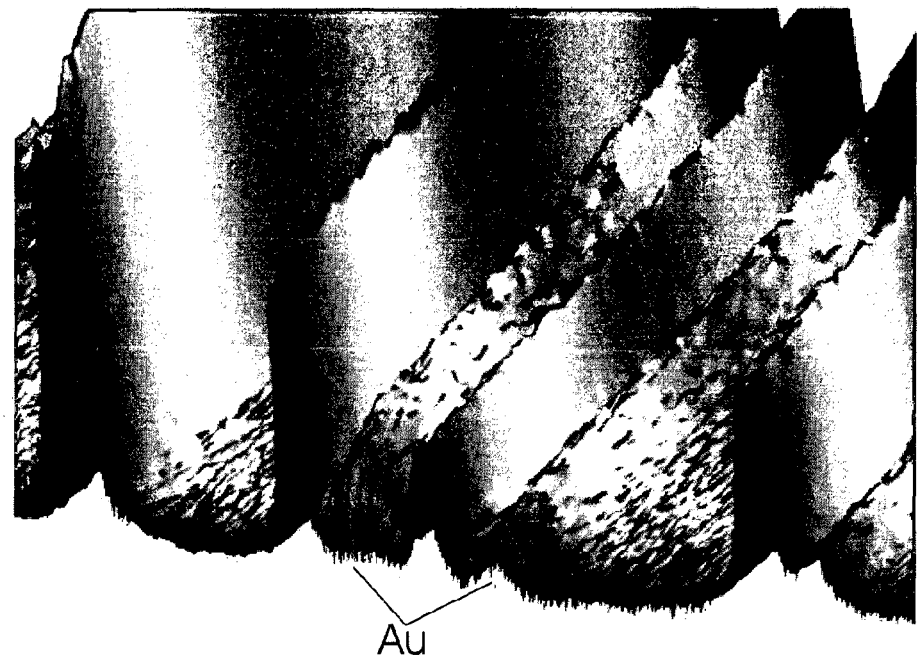
FIG. 14 shows a zoomed view of the Au peaks at 38.2° and 44.4° 2θ for the 8% Au on $TiO_2$ rutile nanorod catalyst particles.

With the use of higher Au loadings, observations were made on the Au structure at lower temperatures. FIG. 14 shows the reduction of the Au peaks from Au (I or II) to Au (0). Further, the intensity of the Au peaks increased only slightly as the temperature was increased from ambient to 810 deg C.

The peak shape profile was also consistent throughout the temperature range. This demonstrated the stability of the Au metal nanoparticles on the surface of the $TiO_2$ rutile nanorod catalyst particles as well as the resistance of the metal nanoparticles to sintering even at high temperatures.

Figure 15:
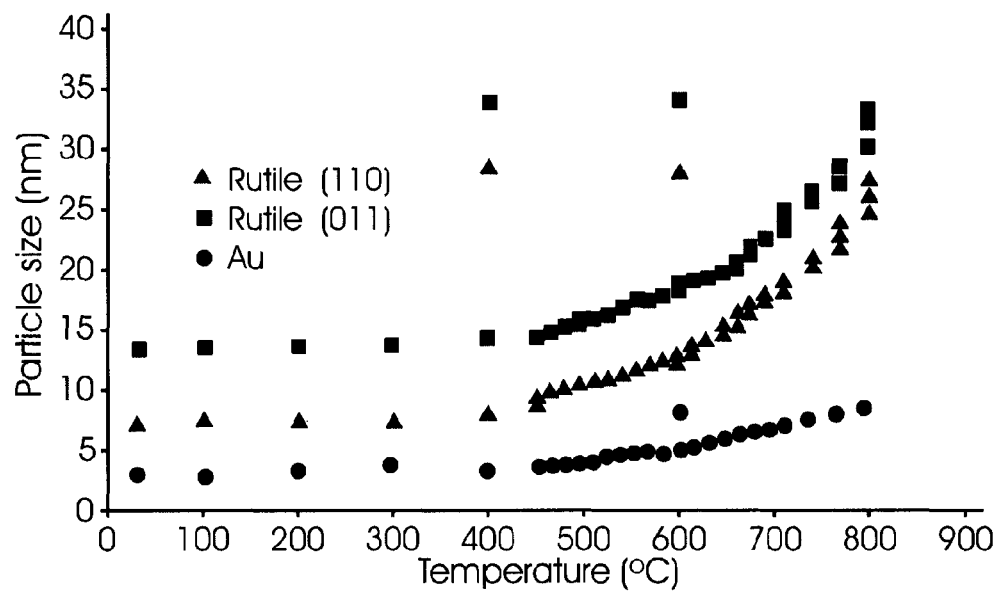
FIG. 15 shows Rietveld refinement results of the Au $TiO_2$ rutile nanorod catalyst particle sizes versus temperature.
Figure 16:
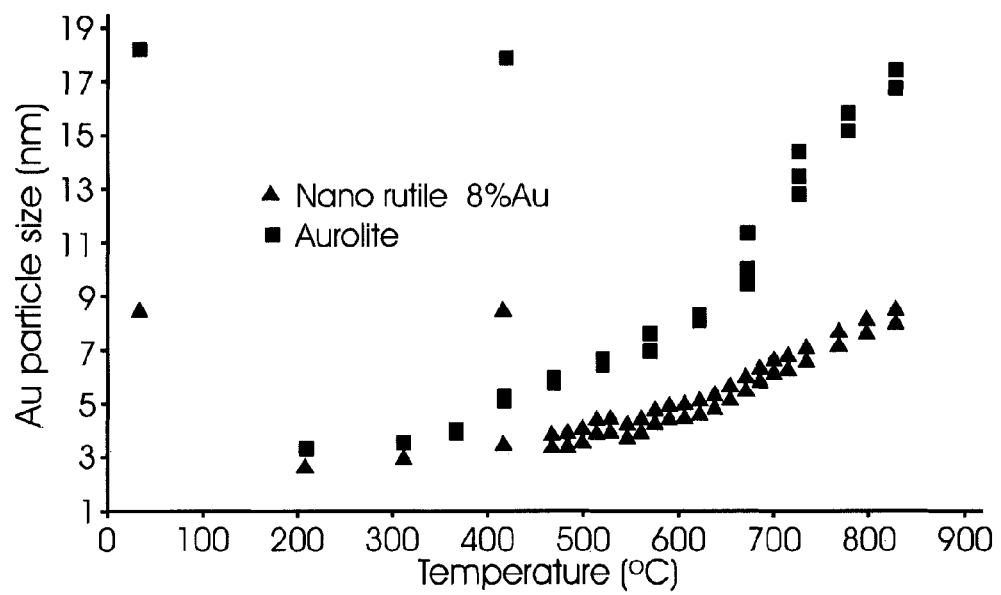
FIG. 16 shows Rietveld refinements comparing the Au $TiO_2$ rutile nanorod catalyst with the commercially available Aurolite catalyst.

The Rietveld refinement results as shown in FIGS. 15 and 16 shows that the Au $TiO_2$ rutile nanorod catalyst particles are more stable and resistant to sintering when compared to the commercially available Aurolite catalyst, even after the Au TiO$_2$ rutile nanorod catalyst particles were exposed to higher temperatures for significantly longer durations. The morphology, along with the thermodynamic stability and high surface area of the particles resulted in a structure that is conducive to thermally stable Au nanoparticles even at high temperatures.

Figure 17:
FIG. 17 shows electron diffraction images showing anisotropic growth of the $TiO_2$ rutile nanorods.

Electron diffraction as shown in FIG. 17 was undertaken in order to determine the arrangement and orientation of the nanorods and to confirm the in-situ PXRD results.

The in-situ PXRD results provided some information about the anisotropic growth of the nanorod structures. The orientation of the nanorods was crucial in order to maintain a high surface area, as well as a desired morphology such that the nanostructure allowed gas to pass easily through it when catalysis was undertaken. Finally, in this embodiment, the dandelion shaped orientation of the nanorods completely inhibit the transfer of Au across the structure as the free end of each nanorod is isolated from adjacent nanorods, thereby isolating the metal nanoparticles from one another.

Figure 18:
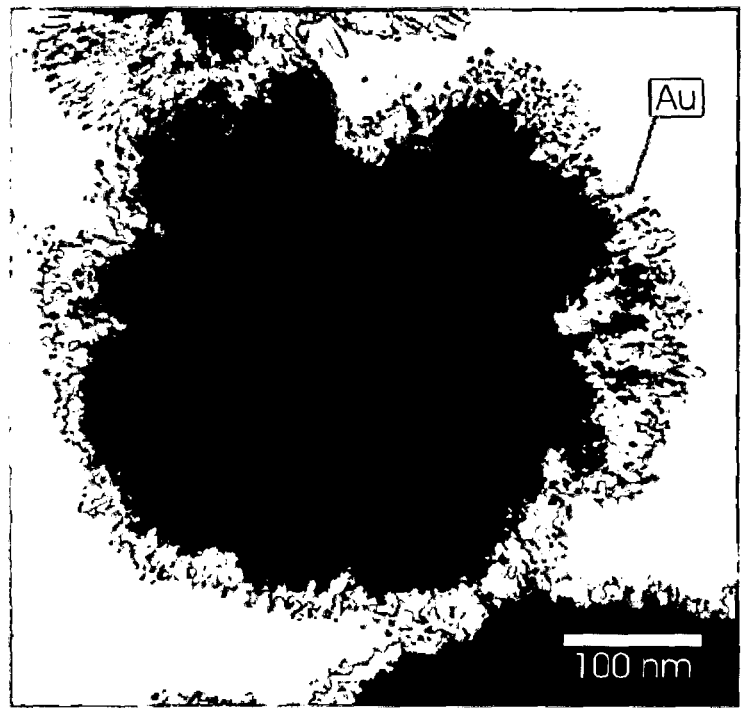
FIG. 18 shows a transmission electron microscope (TEM) image of the 5% Au $TiO_2$ rutile nanorod catalyst particles.
Figure 19:
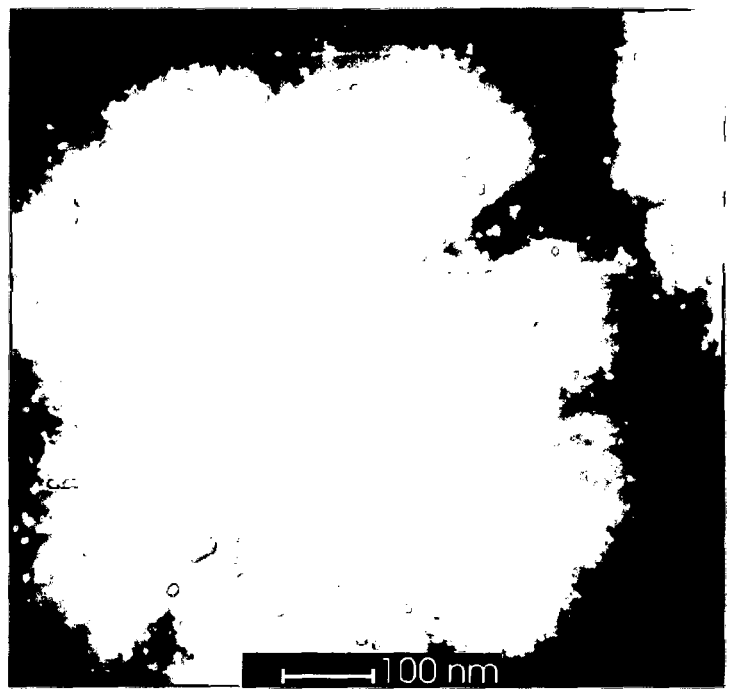
FIG. 19 shows a scanning transmission electron microscopy (STEM) image of the $TiO_2$ rutile nanorod catalyst after exposure to 550 deg C. for 24 hours.
Figure 20:
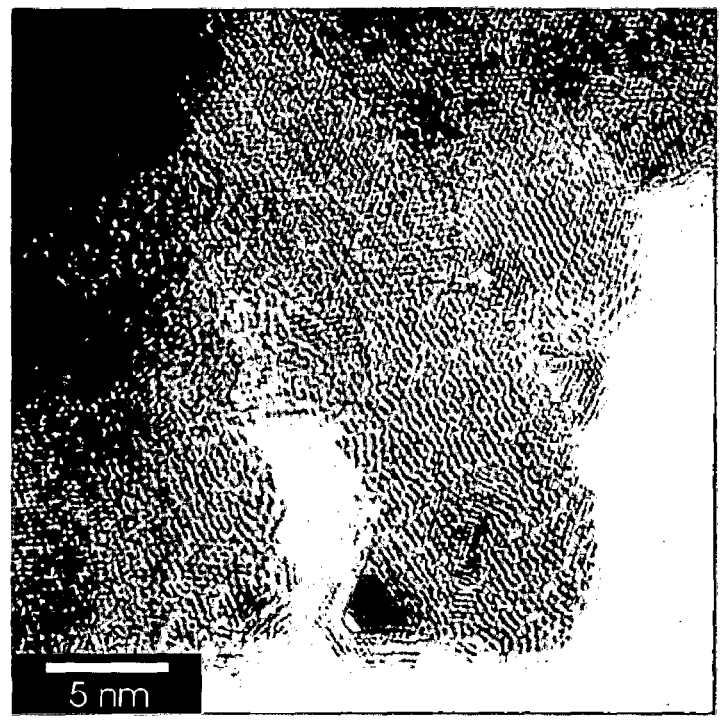
FIG. 20 shows a high resolution transmission electron microscopy (HR-TEM) image of Au nanoparticles on the catalyst after heating to 450 deg C. for 24 hours.
Figure 21:
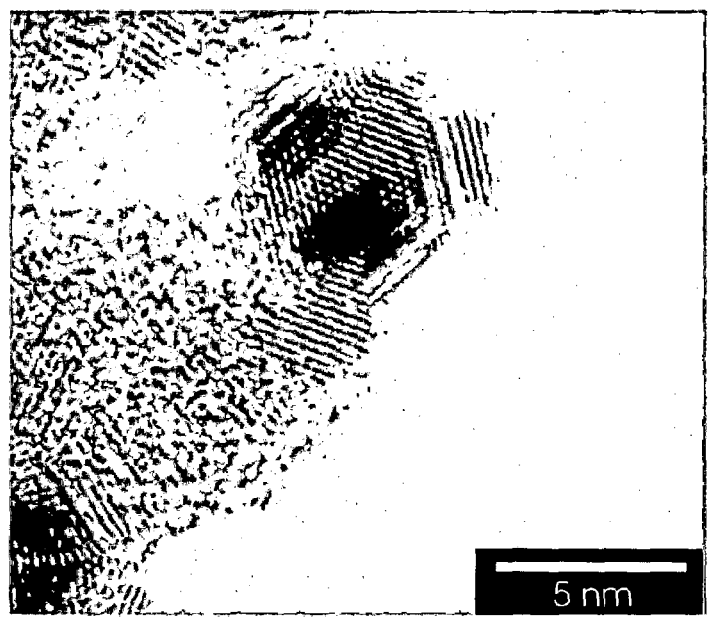
FIG. 21 shows a HR-TEM image of an Au nanoparticle on the catalyst after heating to 450 deg C. for 24 hours.
Figure 22:
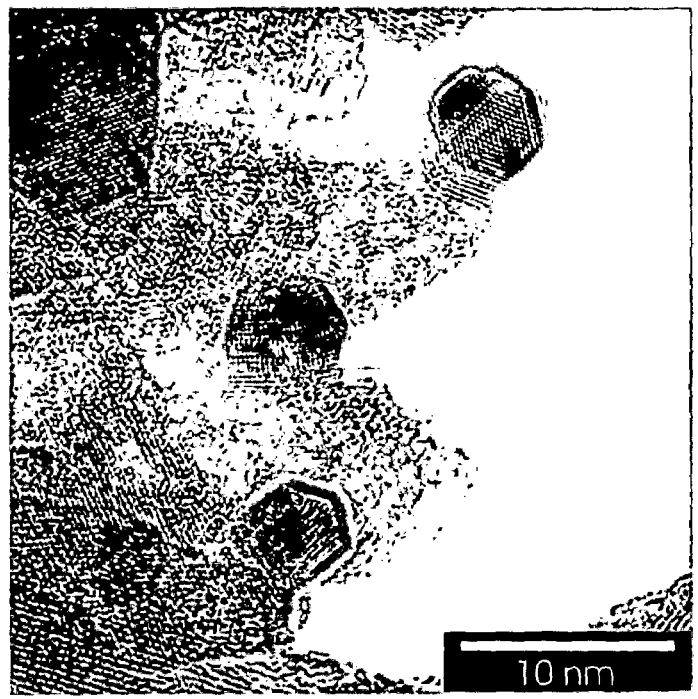
FIG. 22 shows a HR-TEM image of Au nanoparticles on the 5% Au $TiO_2$ rutile nanorod catalyst showing many Au nanoparticles isolated on the ends of the nanorods after heating to 450 deg C. for 24 hours.

Referring to FIGS. 18-20, TEM analysis showed that the nanorods only have a few Au nanoparticles per nanorod. In fact, as is shown in FIGS. 21 and 22, some nanorods were only loaded with a single Au metal nanoparticle. This is an effect of the morphology and gives rise to the high surface area. Thus, in these cases it was impossible for sintering to occur as the Au metal nanoparticles were completely isolated from each other.

FIG. 19 shows the morphology of the Au TiO$_2$ rutile nanorod catalyst particle with the nanorods extending from a central point in a dandelion shaped structure, as determined in the electron diffraction study.

The 5% Au TiO$_2$ rutile nanorod catalyst particles were aged for 5 months to determine if a long period of time negatively affected the Au particle sizes of the catalyst. The catalyst particles, as shown in FIGS. 19 and 20, were left in the dark and stored under atmospheric conditions for 5 months prior to exposure to 550 deg C. for 24 hours followed by TEM analysis. From these Figures it was determined that the ageing process as described above had no effect on the catalyst as the Au nanoparticle sizes were still relatively small, indicating the catalyst's stability.

From the TEM images it appeared that the Au nanoparticles may be positioned on the tips of the nanorods, or possibly inside. Scanning transmission electron microscopy (STEM) and then 3D tomography were used to confirm that the Au nanoparticles were in fact on the tips of the nanorods.

As was revealed from in-situ PXRD data the nanorod structure grew with an increase in temperature whereby the nanorods were extruded from the central point of the dandelion shaped structure outwards. This effect was inhibited when Au was placed on the surface of the nanorod, but still occurred to a small extent as was revealed by quantitative Rietveld refinements on the in-situ PXRD data. However, this extrusion of the nanorods did not have a detrimental effect on the catalyst, as the Au nanoparticles were transported by the nanorods further outward and further away from adjacent nanorods and thus further away from Au nanoparticles located on adjacent nanorods.

This relative isolation of the Au nanoparticles by the nanorods enhanced the stability of the Au nanoparticles, and of the catalyst particle as a whole.

Figure 23:

The Au nanoparticle sizes attained from TEM images were in agreement with the in-situ PXRD results after exposure to comparable temperatures. After thermal exposure, such as that of the catalyst particles from the in-situ diffraction data collection shown in FIG. 23, the Au nanoparticles were still relatively small, with many in the 4-5 nm size range. However, as shown by quantitative Rietveld refinements, there were also a number of larger Au nanoparticles in the range of 5-9 nm as can be seen in FIG. 23.

Many of the larger metal nanoparticles could be attributed to the high Au loadings (8% Au in this case) as the probability that two or more Au nanoparticles will come into contact on a single nanorod was increased with the increased metal nanoparticle loadings.

When the CO oxidation results were considered the TEM results explained what was being observed between the difference in catalytic activity of the fresh, unheated, catalyst particles and the heat treated catalyst particles. The fresh catalysts only consisted of metal nanoparticles less than 5 nm in size. Thus, the activity of the fresh catalyst particles was very high due to all the Au metal nanoparticles being involved in CO conversion.

Without wishing to be bound by the confines of theory, it is believed that the heat treatment of the catalyst particles at temperatures as high as 810 deg C. caused a relatively small number of the Au metal nanoparticles to sinter due to their close proximity to each other (where more than one metal nanoparticle was deposited on a nanorod). This sintering may also be caused due to small changes in the support structure as could be seen from the in-situ PXRD as the nanorods grew in size by small amounts corresponding to a small loss in surface area.

Another reason may be the random placement of the Au nanoparticles onto the TiO$_2$ rutile nanorod support during the synthesis of the catalyst particles. It was shown by 3D tomography that the majority of the Au nanoparticles were deposited on the tips of the nanorods of the support structure. Thus, it was likely that some of the Au nanoparticles would be very close to one another especially when the Au nanoparticle loadings were high, thereby increasing the probability of contact between two or more Au nanoparticles. However, once this initial nanoparticle rearrangement had taken place the nanorod support, as well as the supported metal nanoparticles remained very stable and the catalyst particles could be held at relatively high temperatures for long periods of time without further deactivation.

Figure 24:
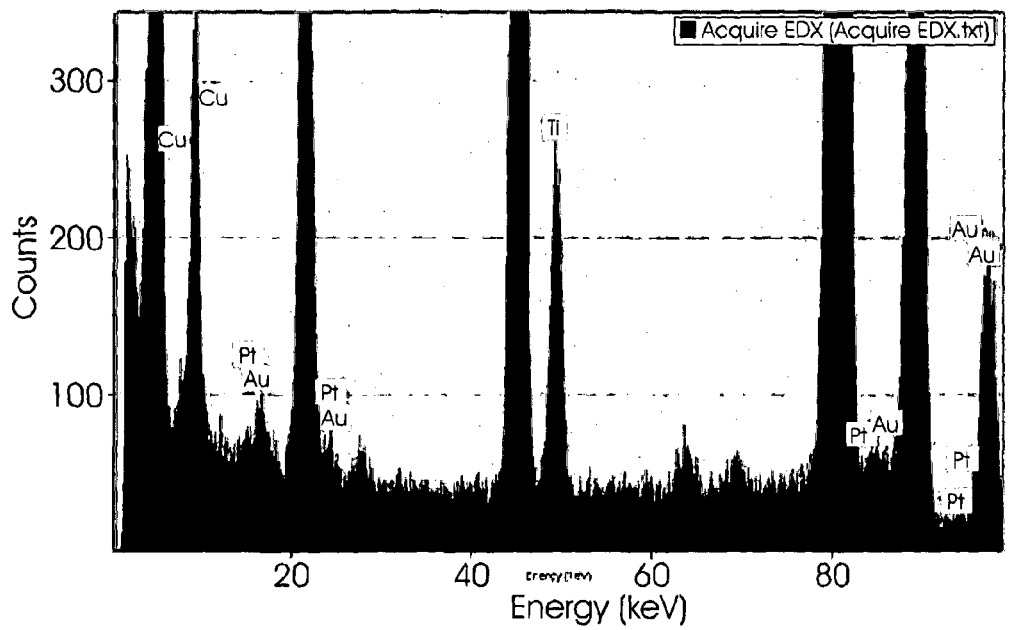
FIG. 24 Energy-dispersive X-ray spectroscopy (EDS) of 1% Au-0.2% Pt $TiO_2$ rutile nanorod catalyst particles showing the presence of both Au and Pt nanoparticles.

EDS was conducted on a 1% Au-0.2% Pt TiO$_2$ rutile nanorod catalyst particle sample, prepared according to the method described above, to determine the position of the Pt metal nanoparticles in relation to the Au metal nanoparticles. The results were inconclusive, but did show that Pt nanoparticles were present on the nanorods. From FIG. 24 it could be seen that both Au and Pt were present, however, it could not be stated with certainty where the metal nanoparticles are positioned with respect to one another due to the close proximity of the molecular weights of Au and Pt.

Catalysis Testing and Catalysis Data

A number of catalysts were tested with all tests being done in triplicate using catalyst particle samples that too were produced in triplicate to test for consistency between the samples.

The testing produced data that in certain instances revealed more about the properties of the catalyst particles. In some cases the testing of the catalyst particles also served as a type of characterization technique as the CO conversion could be related directly to the Au nanoparticle particle size. Thus, changes in the conversion could be related to what had occurred to the sample due to exposure to non-ambient conditions.

Figure 25:
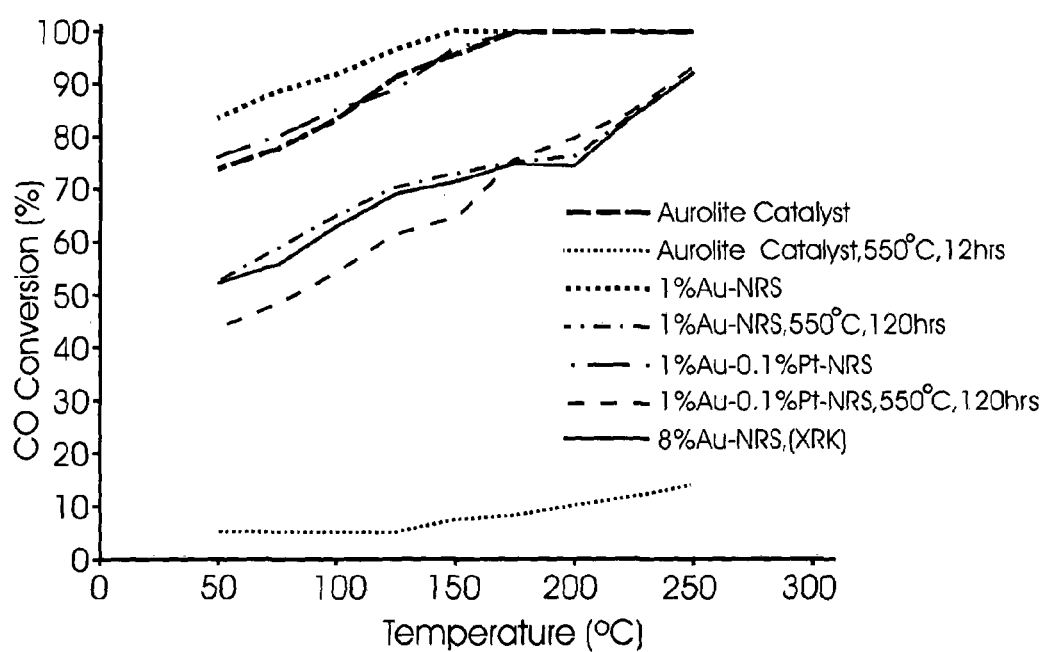
FIG. 25 shows a graph of experimental data for CO oxidation testing of various catalysts.

All catalytic runs were conducted in triplicate and the results averaged to compile FIG. 25.

150 mg of catalyst was used in each case with a gas hourly space velocity of 24000 ml·h$^{-1}$·g$^{-1}$. The gasses were a combination of 5% CO in He and 10% O$_2$ in He. Prior to all data collections the catalysts were fully reduced. Analyses were undertaken at a minimum temperature of 50 deg C. as the thermocontroller error increase with a further decrease in temperature. The commercially available Aurolite catalyst was used as a standard for comparison.

The gas composition used in the catalytic testing of the TiO$_2$ rutile nanorod catalyst particles was significantly higher in CO and O$_2$ compared to gas compositions used commercially. A 5% CO-10% O$_2$ mixture was used while a 1% CO-2% O$_2$ composition is traditionally used in industry. This composition was chosen as the detector used in the experiments provided more accurate results at these compositions. Also, the catalysts would be stressed further, as higher concentrations of CO and O$_2$ required the catalyst to use more of its available active sites to convert both the high flow rate as well as the high CO concentrations.

The triplicate set of Aurolite catalysts were first tested as is, without any exposure to elevated temperatures other than what was experienced during the catalytic test itself. These experiments gave very high activity for the flow rate and reaction temperatures used. The fresh unheated catalysts compared well to the other sets of fresh unheated catalysts, the rate of conversion of the fresh unheated catalysts all being similar. However, once the triplicate set of Aurolite catalysts were heated to 550 deg C. for 12 hours the CO conversions decreased significantly. The Aurolite catalysts had completely deactivated, giving CO conversions of less than 5%. The conversion was almost completely independent of Au and was primarily due to the titania support. This significant deactivation of the set of Aurolite catalysts demonstrated why catalysts of its type have never been applied to auto-catalysts as activity cannot be maintained for long durations after exposure to moderate to relatively high temperatures. In other, separate tests, the Aurolite catalyst was heated at 450 deg C. for 24 hours and tested. Again the catalyst completely deactivated showing no oxidation of CO resulting from Au active sites.

The triplicate set of 1% Au TiO$_2$ rutile nanorod catalysts showed similar CO conversion activity when compared to the fresh unheated Aurolite catalysts. The TiO$_2$ rutile nanorod catalysts were then heated at 550 deg C. for 120 hours (96 hours longer than the heating cycle applied to the Aurolite catalyst). Following this heating cycle, CO conversions showed, on average, approximately a 25% decrease in conversion at 50 deg C. compared to the unheated catalyst. At 150 deg C. the difference in conversion was less than 20%, while at 250 deg C. the difference in conversion was less than 5%. The decrease in CO oxidation was significantly lower for the TiO$_2$ rutile nanorod catalyst particles when compared to the complete deactivation of the Aurolite catalyst. At 250 deg C the heated Aurolite catalyst had a CO conversion of 12%.

The decrease in the CO conversion of the Au/Au—Pt TiO$_2$ rutile nanorod catalysts is best explained from TEM and in-situ diffraction results. TEM images revealed that a small number of the Au nanoparticles sinter forming nanoparticles in a size range dependent on what temperature the catalyst particles were exposed to as well as the duration of exposure. For example, the Au TiO$_2$ rutile nanorod catalyst that was exposed to 810 deg C. reached an Au particle size of 9 nm as shown from Rietveld refinements. While a number of these larger nanoparticles exist, there were many Au nanoparticles that remained relatively small and were responsible for the conversion of CO. The 25% loss in CO conversion at 50 deg C. in the samples heated to 550 deg C. for 120 hours can be attributed to the sintering of a small number of the Au metal nanoparticles and the resulting loss of some active sites by the formation of larger nanoparticles.

The loss of these active sites occurs quite rapidly. From a batch of 1% Au TiO$_2$ rutile nanorod catalyst particles one sample was heated to 550 deg C. for 24 hours and another for 120 hours. No significant change in activity was noted between these samples when they were tested for CO oxidation at 50 deg C. In both cases the catalysts showed a 25% loss in activity compared to fresh unheated TiO$_2$ rutile nanorod catalyst particle sample, even though one sample was exposed to 550 deg C. for 96 hours longer than the other. This result shows that the Au and Au—Pt TiO$_2$ rutile nanorod catalyst particles may be stable indefinitely once the initial loss of activity has taken effect.

The set of 1% Au-0.1% Pt TiO$_2$ rutile nanorod catalysts were heated to 550 deg C. for 120 hours. After the heating cycle the 1% Au-0.1% Pt TiO$_2$ rutile nanorod catalyst particles gave a lower activity when compared to the 1% Au TiO$_2$ rutile nanorod catalyst. For supported Pt catalysts, the conversion of CO only occurs at temperatures in excess of 150 deg C. and higher. Thus, at the lower temperatures where the initial CO conversion data was collected the platinum will most certainly have no effect on CO conversion. After 150 deg C. the conversion took a small upward movement at 175 deg C.

The 8% Au TiO$_2$ rutile nanorod catalysts (from the in-situ PXRD data collection taken from the XRK chamber) were tested for catalytic activity. Once the in-situ diffraction data collection was completed the sample chamber was removed from the diffractometer. Samples from previous in-situ data collections were not analysed for CO oxidation as it was incorrectly assumed that the catalyst particles would not be able to withstand temperatures over 800 deg C. However, it was decided to test the final XRK sample and the results are shown in FIG. 25.

The test results showed that the catalyst particles were still active, albeit with an initial loss of activity similar to the other Au and Au—Pt TiO$_2$ rutile nanorod catalyst particles that had been exposed to 550 deg C. for 120 hours. The activity of the catalyst particles showed that the initial loss of activity occurs rapidly, perhaps from a rearrangement of the Au nanoparticles as seen in the TEM images as a number of different shaped nanoparticles were observed. Once this initial loss of activity had taken place the catalyst particle was able to remain stable even after exposure to extreme temperatures for long periods of time. The catalyst was able to replicate within experimental error the CO conversions achieved by the 1% Au TiO$_2$ rutile nanorod catalyst particles that were exposed to 550 deg C. for 120 hours. The CO oxidation results are reinforced by the findings of in-situ diffraction, the resulting Rietveld refinements as well as TEM results.

The CO oxidation reaction was selected by the inventors to compare the performance of the catalyst particles according to the present invention with the performance of certain commercially available catalysts. The CO oxidation reaction is known to be extremely sensitive and is therefore a good indicator of catalyst performance in many respects.

However, Au nanocatalysts are known to have very high activities in a number of other important industrial reactions, and it will be appreciated by one skilled in the art that the catalyst of the present invention will also find application in these reactions. Some of the these reactions and uses include the oxidation of hydrocarbons, the reduction of NO$_x$, the water-gas-shift reaction, H$_2$O$_2$ production from H$_2$ and O$_2$, the removal of CO from hydrogen steams, the epoxidation of alkenes, the oxidative destruction of hydrochlorides, the oxidation of $CH_4$, the photocatalytic splitting of water, for Fisher Tropsch, the reactions in fuel cells, the synthesis of controlled carbon nanotubes, and for use in dye sensitised solar cells.

The invention claimed is:

1. A titanium dioxide catalyst particle, for use in catalysing reactions after exposure of the particle to temperatures above 550 deg C, the particle comprising rutile nanorods extending radially from a central point, each nanorod having a free end spaced from adjacent nanorods, the particle including metal nanoparticles deposited at the free ends of the nanorods selected from the group consisting of gold, nickel, copper, iron, platinum, palladium, ruthenium, rhodium, and/or alloys thereof, wherein the particle has a BET surface area of between about 50 and about 125 $m^2/g$.

2. A catalyst particle according to claim 1, wherein the particle has a BET surface area of between about 75 $m^2/g$ and about 115 $m^2/g$.

3. A catalyst particle according to claim 1, wherein the particle has a BET surface area of about 100 $m^2/g$.

4. A catalyst particle according to claim 1, wherein the metal nanoparticles are selected from the group consisting of gold, platinum, and/or alloys thereof.

5. A catalyst particle according to claim 4, wherein the metal nanoparticles are gold nanoparticles.

6. A catalyst particle according to claim 1, wherein the metal nanoparticles are present at loadings of between about 0.1% and about 10% by weight of the particle.

7. A catalyst particle according to claim 6, wherein the metal nanoparticles are present at loadings of between about 0.5% and about 5% by weight of the particle.

8. A catalyst particle according to claim 6, wherein the metal nanoparticles are present at loadings of about 1%.

9. A catalyst particle according to claim 1, wherein the catalysed reaction is selected from a group consisting of oxidation of CO, oxidation of hydrocarbons, reduction of $NO_x$, water-gas-shift reaction, $H_2O_2$ production from $H_2$ and $O_2$, removal of CO from hydrogen steams, epoxidation of alkenes, oxidative destruction of hydrochlorides, and/or the oxidation of $CH_4$.

10. A catalyst particle according to claim 9, wherein the catalysed reaction is the oxidation of CO.

11. A catalyst particle according to claim 1, wherein the particle has a substantially spherical dandelion shaped configuration.

12. A catalyst particle according to claim 1, wherein the nanorods are of substantially similar length.

13. A catalyst particle according to claim 1, wherein the nanorods are comprised of substantially phase pure rutile.

14. A catalyst particle according to claim 1, wherein the particle has a CO oxidation conversion at about 50 deg C of more than 50%, compared to the CO oxidation conversion of an unheated catalyst particle, after heating at a temperature of between about 550 deg C and about 800 deg C for at least 24 hours.

15. A catalyst particle according to claim 14, wherein the particle has a CO oxidation conversion at about 50 deg C of more than about 65%, compared to the CO oxidation conversion of an unheated catalyst particle, after heating at a temperature of about 550 deg C for at least 120 hours.

16. A catalyst particle according to claim 14, wherein the particle has a CO oxidation conversion at about 50 deg C of about 75%, compared to the CO oxidation conversion of an unheated catalyst particle, after heating at a temperature of about 800 deg C for at about 200 hours.

17. A catalyst composition comprising a plurality of catalyst particles according to claim 1.

18. A catalyst composition according to claim 17, wherein the particles are fixed to a support.

19. A catalyst composition according to claim 17, wherein the particles are in solution or in suspension.

20. A method of catalysing reactions comprising the step of exposing a reagent or reagents to a catalyst particle according to claim 1, or a catalyst composition according to claim 17, the catalyst particle having been previously exposed to temperatures above 550 deg C.

* * * * *